United States Patent [19]

Umezawa et al.

[11] 4,147,774

[45] Apr. 3, 1979

[54] ANTIBIOTIC SPORAMYCIN

[75] Inventors: Iwao Umezawa, Tokyo; Kanki Komiyama; Hideo Takeshima, both of Yokohama, all of Japan

[73] Assignee: The Kitasato Institute, Tokyo, Japan

[21] Appl. No.: 814,665

[22] Filed: Jul. 11, 1977

[30] Foreign Application Priority Data

Jul. 10, 1976 [JP] Japan .................................. 51-81470

[51] Int. Cl.$^2$ ............................................. A61K 35/00
[52] U.S. Cl. .................................... 424/118; 424/116; 195/80 R
[58] Field of Search .............. 424/116, 118; 195/80 R

[56] References Cited

PUBLICATIONS

Umezawa et al., J. of Antibiotics 29(11), pp. 1249–1251 (11-1976).
Komiyama et al. J. of Antibiotics 30 (3), pp. 207–208 (3-1977).

Primary Examiner—Jerome D. Goldberg
Attorney, Agent, or Firm—Young & Thompson

[57] ABSTRACT

A novel antibiotic sporamycin has both anti-transplanted tumor and antibacterial activity and is produced by culturing a microorganism of the genus Streptosporangium, particularly *Streptosporangium pseudovulgare* PO-357 FERM-P No. 3571, ATCC No. 31308.

2 Claims, 4 Drawing Figures

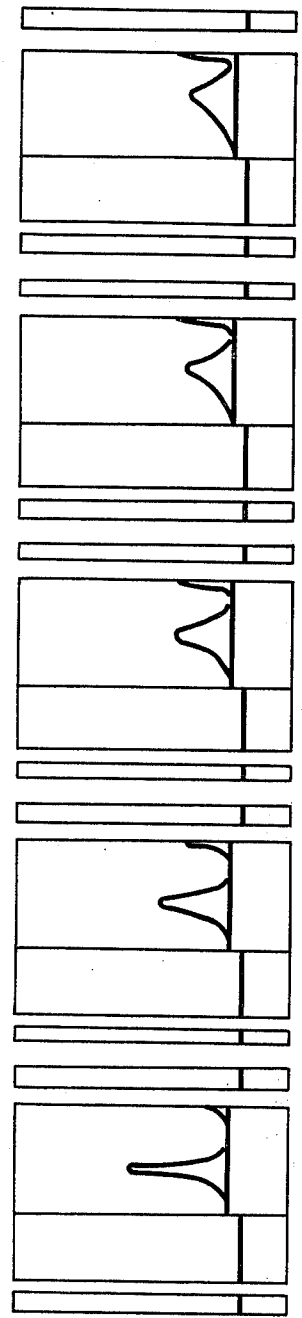
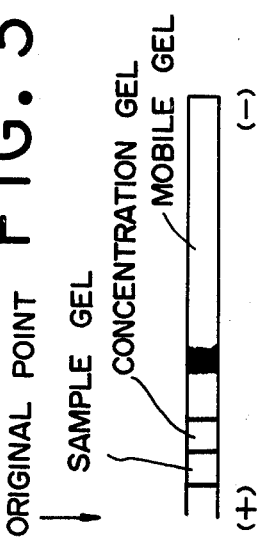

ANTIBIOTIC SPORAMYCIN

This invention relates to a novel anti-transplanted tumor antibiotic sporamycin and a method for preparing the same.

The novel antibiotic of the present invention has the following physico-chemical properties.

Figure 1:
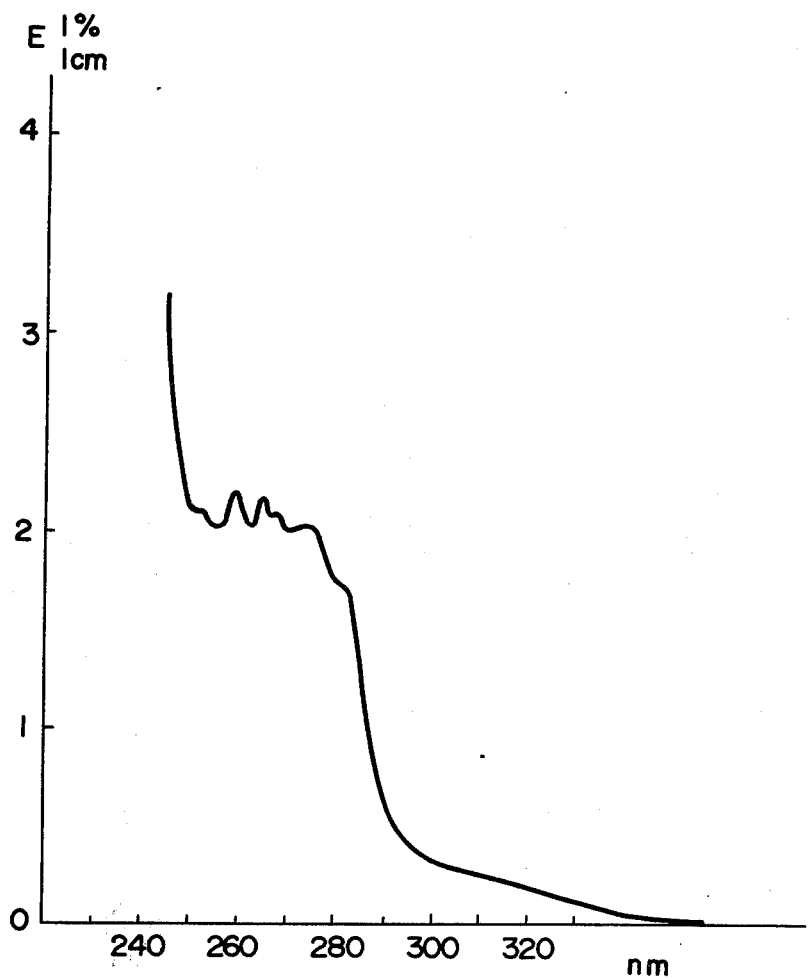
Figure 2:
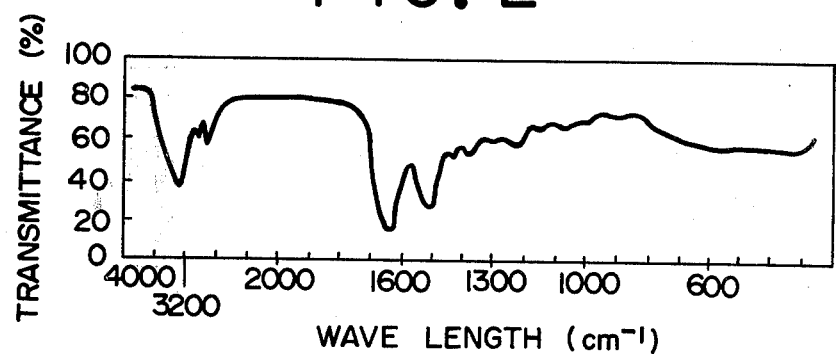

(1) comprised by carbon, hydrogen nitrogen and oxygen; elemental analysis of C:44.72–47.38%, H:66.4–6.88% and N:13.93–15.0%;

(2) ultraviolet absorption spectrum: as shown in FIG. 1; absorption peaks at 285 nm (shoulder), 276 nm, 267 nm, 265 nm, 258 nm and 253 nm in an aqueous solution or in acidic solution, and at 290 nm in alkaline solution;

(3) infrared absorption spectrum: as shown in FIG. 2, absorption peaks at 3320 cm$^{-1}$, 1640 cm$^{-1}$ and 1520 cm$^{-1}$ in KBr;

(4) white powder;

(5) solubility: soluble in water, insoluble in organic solvent such as methanol, ethanol and acetone;

(6) color reaction: positive for Folin-Lowry, Ehrlich and biuret reactions, weakly positive for ninhydrin reaction, negative for Molisch, Fehling, Tollens and anthrone reactions;

(7) molecular weight: 10,500–13,000;

(8) amino acid analysis by 6 N HCl hydrolysis (110° C., 15 hrs.). At least 12 kinds of amino acids were detected: lysine, aspartic acid, threonine, serine, glutamic acid, glycine, alanine, valine, isoleucine, leucine, tyrosine and phenylalanine.

(9) basic substance detected by mobility for cathode on paper electrophoresis (250 V., 3.5 hrs.) using acetate buffer (pH 4.0) or phosphate buffer (pH 8.0); and

(10) m.p.: become brown at 220–225° C., and carbonized at increased temperature;

(11) $[\alpha]_D^{20}$: approximately $-56°$ (C=0.5, H$_2$O); and

(12) impermeable through Cellophane membrane and precipitated by 80% saturated ammonium sulfate.

Biological properties of sporamycin are as follows:

(1) Antimicrobial activity:

Antibacterial and antifungal spectra indicated as minimum inhibitory concentration (MIC) by agar dilution method are shown in Table 1.

Table 1.

| Antimicrobial activity of Sporamycin. | | |
|---|---|---|
| Test organism | | MIC (mcg/ml) |
| Staphyloccus aureus | FDA 209P | 0.1 |
| Staphylococcus aureus | JC-1 | 0.05 |
| Staphylococcus aureus | FS 1277 | 2.1 |
| Bacillus subtilis | PCI 219 | 2.1 |
| Bacillus cereus | IFO 3001 | 10.3 |
| Sarcina lutea | PCI 1001 | 50.0 |
| Mycobacterium smegmatis | ATCC 607 | >100 |
| Escherichia coli | NIHJ | >100 |
| Shigella sonnei | E 33 | >100 |
| Salmonella typhimurium | | >100 |
| Klebsiella pneumoniae | PCI 602 | >100 |
| Aerobacter aerogenes | ATCC 9621 | >100 |
| Pseudomonas aeruginosa | P-3 | >100 |
| Candida albicans | | >500 |
| Saccharomyces sake | | >500 |
| Aspergillus nigar | | >500 |
| Aspergillus fumigatus | | >500 |
| Trichophyton interdigitate | | >500 |
| Trichophyton mentagrophytes | | >500 |
| Piricularia oryzae | | >500 |
| Cryptococcus neoformans | | >500 |
| Alternaria kikuchiana | | >500 |
| Sclerotinia cinerea | | >500 |
| Penicillium notatum | | >500 |

(2) Toxicity: acute toxicity (LD$_{50}$) in mice; approximately 15 mg/kg (i.p.) and approximately 13 mg/kg (i.v.).

(3) Antitumor activity:

[I] Experimental method.

(a) Tumor transplanation.

1. CDF$_1$ mice were inoculated intraperitoneally with 1 × 10$^5$ ascites cells of leukemia L-1210 or P-388 cells.

2. dd Mice were inoculated intraperitoneally with 2 × 10$^6$ cells of Ehrlich ascites carcinoma.

3. dd Mice were implanted subcutaneously with small pieces of tumor tissues of sarcoma-180 (2 mm$^3$) at the axillary region.

(b) Treatment.

1. After 24 hours of tumor cell inoculation, sporamycin was administered intraperitoneally or intravenously once a day for 9 days.

2. After 24 hours of tumor cell inoculation, sporamycin was injected intraperitoneally or intravenously one time.

[II] Evaluation.

1. The therapeutic efficacy of sporamycin on leukemia L-1210, P-388 and Ehrlich ascites carcinoma was determined by observing the survival days of the mice and is given by the following:

$$\frac{\text{average survival days of treated group (T)}}{\text{average survival days of control group (C)}} \times 100 = \text{survival ratio (T/C \%)}$$

2. The effect of sporamycin on solid tumor sarcoma-180 was determined by measuring the maximum and minimum diameters of the subcutaneous tumor with calipers and is given as a percentage of tumor growth inhibition by the following:

$$100 - [\frac{\text{average tumor size of treated group (S)}}{\text{average tumor size of control group (W)}}] \times 100 = \text{growth inhibition (S/W \%)}$$

[III] Results.

The effects of sporamycin on leukemia L-1210, leukemia P-388, Ehrlich ascites carcinoma and solid type sarcoma-180 tumor are shown in Tables 2, 3, 4 and 5, respectively.

Table 2.

| Effect of Sporamycin on Leukemia L-1210. | | | |
|---|---|---|---|
| Treatment schedule (i.p.) | Total dose (mg/kg) | Average survival days | Survival ratio (T/C %) |
| control | | 8.0 | 100 |
| | 15 | 12.6 | 157 |
| | 10 | 12.7 | 159 |
| administered | 7.5 | 10.7 | 134 |
| daily | 5.0 | 11.9 | 148 |
| (1–9th) | 3.8 | 11.6 | 145 |
| | 2.5 | 11.4 | 143 |
| | 1.3 | 10.6 | 132 |
| single | 10 | 11.4 | 143 |
| administration | 7.5 | >16.6 | >198* |
| (day 1) | 5.0 | 11.3 | 141 |
| | 3.8 | 10.9 | 136 |
| | 2.5 | 11.4 | 143 |
| | 0.9 | 11.3 | 141 |

*one mouse survived over 60 days (period of the experiments)

Table 3.
Effect of Sporamycin on Leukemia P-388.

| Treatment schedule (i.p.) | Total dose (mg/kg) | Average survival days | Survival ratio (T/C %) |
|---|---|---|---|
| control | | 12.0 | 100 |
| | 15 | 19.3 | 161 |
| | 10 | 18.9 | 157 |
| administered | 7.5 | 17.6 | 146 |
| daily | 5.0 | 17.0 | 142 |
| (1–9th) | 3.8 | 17.0 | 142 |
| | 2.5 | 15.7 | 131 |
| | 1.9 | 15.9 | 132 |
| | 10 | 20.9 | 172 |
| | 7.5 | 17.6 | 145 |
| single | 5.0 | >21.9 | >181* |
| administration | 3.8 | >21.9 | >181* |
| (day 1) | 2.5 | 19.1 | 158 |
| | 0.9 | 17.0 | 140 |

*in each case one mouse survived over 60 days (period of the experiments)

Table 4.
Effect of Sporamycin on Ehrlich Ascites Carcinoma.

| Treatment schedule (i.p.) | Total dose (mg/kg) | Average survival days | Survival ratio (%) | 60 days survivors total No. treated |
|---|---|---|---|---|
| control | | 26.1 | 100 | 0/7 |
| | 10 | 50.1 | 192 | 0/7 |
| | 7.5 | >52.4 | >201 | 3/7 |
| | 5.0 | >54.7 | >210 | 4/7 |
| administered | 3.8 | >54.0 | >207 | 3/7 |
| daily | 2.5 | >55.0 | >211 | 4/7 |
| (1–9th day) | 1.9 | >59.6 | >228 | 6/7 |
| | 1.3 | >52.6 | >201 | 4/7 |
| | 10 | >38.7 | >157 | 4/7 |
| | 7.5 | >51.7 | >210 | 5/7 |
| single | 5.0 | >52.6 | >214 | 5/7 |
| administration | 3.8 | >49.9 | >203 | 4/7 |
| (day 1) | 2.5 | >55.4 | >225 | 6/7 |
| | 1.9 | >44.4 | >181 | 3/7 |
| | 1.3 | >35.4 | >144 | 2/7 |

Table 5.
Effect of Sporamycin on Sarcoma-180.

| treatment schedule (i.v.) | Total dose (mg/kg) | Growth Inhibition (%) 8th day | 13th day | 17th day | Number of mice cured |
|---|---|---|---|---|---|
| control | | 0 | 0 | 0 | 0 |
| | 15 | 82 | 80 | 86 | 0 |
| | 10 | 67 | 68 | 75 | 2 |
| | 7.5 | 54 | 58 | 65 | 3 |
| daily | 5.0 | 47 | 53 | 55 | 2 |
| administered | 3.8 | 42 | 45 | 53 | 2 |
| (1–9th day) | 2.5 | 27 | 23 | 27 | 3 |
| | 10 | 97 | 99 | 99 | 1 |
| | 7.5 | 83 | 83 | 85 | 3 |
| single | 5.0 | 56 | 57 | 60 | 3 |
| dose | 3.8 | 50 | 53 | 62 | 3 |
| (day 1) | 2.5 | 37 | 49 | 55 | 4 |

Increased lifespan has also observed when sporamycin was administered intraperitoneally in B-16 melanoma and Lewis lung carcinoma bearing mice.

As hereinabove explained, sporamycin has an antibacterial activity, as well as a remarkable antitumor activity on various experimental tumors in mice by both intravenous and intraperitoneal injection. Toxicity ($LD_{50}$) of sporamycin is median as compared with known other antitumor substances and sporamycin is effective even at a considerably lower dose value than its $LD_{50}$ value.

There are some basic polypeptides with antitumor activities similar to sporamycin, i.e., Actinacarcin [J. Antibiotics, 27, 994 (1974)], phenomycin [j. Antibiotics, Ser. A, 20, 210 (1967)] and mirolidine [Mycology and Mycosis, 7, 272 (1966)]. However, actinocarcin and phenomycin have no antibacterial activity and different ultraviolet absorption spectra from that of sporamycin. Also mirolidine differs from sporamycin as to its toxicity value and ultraviolet absorption spectrum. Therefore sporamycin is defined as a novel antibiotic.

Sporamycin is produced by culturing a microorganism belonging to genus Streptosporangium which produces antibiotic sporamycin and isolating it from the culture broth.

A species of microorganism which produces sporamycin is, for example, *Streptosporangium* sp. strain PO-357 isolated from a soil sample in Setagaya-ku, Tokyo, Japan.

The taxonomic properties of this strain PO-357 are as follows:

1. Morphological properties.

Microscopic examination revealed that the aerial mycelium is straight with most sporangia on the top of the mycelium. Size of sporangium is 5–10μ, mean 7.5μ in diameter. Length of sporangia bearing aerial hyphae is short and mostly about 3μ. Spores are round or ovoid with a smooth surface and a diameter of 0.9–1.4μ. Flagella are not observed.

2. Cultural characteristics on various media.

Observation at 27° C., 10–14 days cultivation.

| Medium | Growth | Reverse | Aerial mycelium | Soluble pigment |
|---|---|---|---|---|
| Sucrose-nitrate agar | poor | pale orange | milk white | none |
| Glucose-asparagine agar | poor | pale yellow | milk white | none |
| Glycerol-asparagine agar | poor | pale yellow | milk white | none |
| Inorganic salt-starch agar | poor | brownish white–white | milk white | none |
| Tyrosine agar | moderate | pale orange | pale orange | none |
| Nutrient agar | moderate-good | orange | orange | none |
| Yeast extract-malt extract agar | good | orange | orange | none |
| oatmeal agar | good | orange | orange | none |

3. Physiological properties.

(1) Growth temperature: possible at 43° C., optimum growth at about 27°–30° C.
(2) Melanin production: negative on tyrosine agar.
(3) Liquefaction of gelatine: positive.
(4) Hydrolysis of starch: positive.
(5) Peptonization of milk: positive.
(6) $H_2S$ formation: negative.
(7) Nitrate reduction: positive.

4. Utilization of carbon source.

Observed on Pridham Gottlieb agar medium containing 0.05% of yeast extract.

Utilization: D-glucose, L-arabinose, D-xylose, D-mannose.

Probable utilization: D-galactose, D-raffinose, L-rhamnose, D-fructose.

No utilization: inositol, saccharose.

5. Cell wall composition.

Analysis of cell walls was made by the method of Becker et al.

[Appl. Microbiol., 13, 236–243 (1965)].

| DAP* | glycine | arabinose | galactose |
|---|---|---|---|
| meso type | —** | — | — |

*diaminopimelic acid
**—:not detected

Various taxonomic properties hereinabove clearly reveal the strain PO-357 as a microorganism belonging to genus Streptosporangium.

Among known species, *Streptosporangium pseudovulgare* Nonomura [J. Ferm. Tech. Japan, 47, 701–709 (1969)] is closely related to the strain PO-357, but there are differences, especially in the color of the aerial mycelium and in their biological activities. Thus, strain PO-357 is designated as *Streptosporangium pseudovulgare* PO-357. The strain was deposited in the Institute for Microbial Industry, Agency of Industrial Science and Technology, Japan, and assigned deposit number FERM-P No. 3571.

In this invention, not only *Streptosporangium* sp. PO-357 but also the natural or artificial mutants thereof, obtained by ultraviolet, X-ray, radiation or chemical mutagens, as well as the microorganisms belonging to genus Streptosporangium having sporamycin producing activity, can be utilized in the production of sporamycin.

In the present invention, the cultivation may be carried out in conventional media.

For the carbon sources of a medium, assimilable carbohydrates such as glucose and starch can be used. For the nitrogen source, organic nitrogen sources such as peptones and meat extract can be used. Inorganic substances such as calcium, sodium or magnesium salts can also be added to the medium.

The cultivation can preferably be performed under aerobic conditions such as shaking culture or submerged aeration culture at pH 6.8–7.0 at 27° C. for about 40–70 hours.

Since sporamycin is a basic high molecular substance, conventional isolation procedures can be used.

An embodiment of the isolation and purification procedures for sporamycin is given hereinbelow.

To a culture filtrate, ammonium sulfate is added to 90% saturation and allowed to stand overnight at 5° C. The sediment formed is dissolved in water and dialyzed in a Cellophane tube against several changes of ice water. The dialysis residue is centrifuged and the insoluble material is discarded. The solution is applied to a column of diethylaminoethyl cellulose equilibrated with 1/500 M phosphate buffer at a pH of about 7–8. The column is eluted with a linear gradient of increasing sodium chloride concentration. To an eluted active fraction is added ammonium sulfate. The precipitate formed is dissolved in water, dialyzed to desalt, and rechromatographed on a diethylaminoethyl cellulose column equilibrated with 1/500 M phosphate buffer at pH 5.4, which is eluted with a linear gradient of increasing sodium chloride concentration. The active fractions are collected and ammonium sulfate is added to precipitate the active substance. The precipitate is dissolved in water, dialyzed using Cellophane membrane and applied to a column of Sephadex G-75 (trademark), which is eluted with water. The thus-eluted active fraction is lyophilized to obtain sporamycin as a white powder.

Sporamycin is assayed by a conventional microbioassay using *Staphylococcus aureus* as a test organism.

The following example illustrates the present invention but is not to be construed as limiting the scope of the invention. Example.

One hundred milliliters of Waksman medium (glucose 2.0%, dried yeast extract 0.3%, peptone 0.5%, calcium carbonate 0.3%, meat extract 0.5% and sodium chloride 0.5% by weight, pH 7.0) was placed in a 500 ml Sakaguchi flask and sterilized at 121° C. for 15 minutes. *Streptosporangium pseudovulgare* PO-357 FERM-P No. 3571 was inoculated thereto and reciprocally shake-cultured (120 strokes/min.) at 27° C., for 96 hours.

Ten milliliters of the cultured broth was inoculated in a pre-culture medium (glucose 0.2%, starch 1.5%, dried yeast extract 0.15%, peptone 0.25%, calcium carbonate 0.25% and meat extract 0.3% by weight, pH 7.0) and cultured for 48 hours under the same conditions as above. The cultured seed was inoculated into two 30-liter jar-fermenters containing 20 liters of the above Waksman medium and aerobically cultured with stirring for 44 hours, at 27° C., 250 r.p.m. under aeration (15 l./min.), to obtain the cultured broth containing sporamycin.

The broth was centrifuged to remove the mycelia, calcium carbonate and other solid materials. To the resulting culture filtrate (35 l.) were added 22 kg of ammonium sulfate, stirred and allow to stand at 5° C. for 20 hours in darkness. The precipitate was collected by suction filtration on Celite and dissolved in water. After filtration, the Celite was discarded and ammonium sulfate was added to the filtrate to precipitate the active substance. The sediment was dialyzed for 3 days in a Cellophane tube against several changes of ice water. The dialysate was applied to a column of diethylaminoethyl cellulose (60×5.5 cm) equilibrated with 1/500 M phosphate buffer at pH 7.5. The column was eluted with a linear gradient of increasing sodium chloride concentration and the eluate was collected as fractions each of 15 ml. Ammonium sulfate was added to combined fractions Nos. 28–61. The solution was centrifuged. The precipitate was dissolved in a minimum volume of water and was dialyzed in Cellophane tube against ice water for 3 days.

The dialyzed solution was placed on a diethylaminoethyl cellulose column (55×5.5 cm) previously equilibrated at pH 7 with 1/500 M phosphate buffer. A linear-gradient-increasing sodium chloride concentration was applied to the column. Fractions of 15 ml each were collected. Fractions Nos. 26–58 were pooled and ammonium sulfate was added to precipitate the active principle. The solution was placed in a Cellophane tube and was dialyzed against ice water. The dialyzed solution was applied to a Sephadex G-75 column (75×2.7 cm) which was eluted with water and the active eluate was lyophilized to obtain sporamycin as white powder (585 mg.).

As shown in FIG. 4, the ultracentrifugal pattern of the thus-obtained sporamycin powder at 52,000 r.p.m., at 1 to 65 minutes gave a single Schlieren peak. By disc electrophoresis on polyacrylamide gel, a well defined single band was observed as shown in FIG. 3.

What is claimed is:

1. An antibiotic sporamycin of the following properties:

(1) comprised by carbon, hydrogen, oxygen and nitrogen;
elemental analysis: C: 44.72–47.38%, H: 6.4–6.88%, N: 13.99–15.0%;

(2) ultraviolet absorption spectrum: as shown in FIG. 1; absorption peaks at 285 nm (shoulder), 276 nm, 267 nm, 265 nm, 258 nm and 253 in an aqueous and 0.1 N HCl solution;
peak at 290 nm in 0.1 N NaOH solution;
(3) infrared absorption spectrum: as shown in FIG. 2; absorption peaks at 3320 cm$^{-1}$, 1640 cm$^{-1}$ and 1520 cm$^{-1}$ in KBr;
(4) white powder;
(5) solubility: soluble in water, insoluble in methanol, ethanol and acetone;
(6) color reaction:
positive: Folin-Lowry, Ehrlich and biuret reactions,
weakly positive: ninhydrin reaction,
negative: Molisch, Fehling, Tollens and anthrone reactions;
(7) molecular weight: 10,500–13,000;
(8) amino acid analysis by 6N HCl hydrolysis (110° C., 15 hrs.): at least 12 kinds of amino acids: lysine, aspartic acid, threonine, serine, glutamic acid, glycine, alanine, valine, isoleucine, leucine, tyrosine and phenylalanine;
(9) basic substance;
(10) melting point: became brown at 220°–225° C., carbonized at increased temperature; and
(11) $[\alpha]_D^{20}$: approximately −56° (C=0.5, H$_2$O).

2. A process for production of antibiotic sporamycin as defined in claim 1 which comprises culturing the microorganism *Streptosporangium pseudovulgare* PO-357 FERM-P No. 3571, ATCC No. 31308, in a nutrient medium until substantial antibiotic activity is imparted to said medium, and isolating the antibiotic sporamycin from the cultured medium.

* * * * *